(12) United States Patent
Birge et al.

(10) Patent No.: US 11,998,443 B2
(45) Date of Patent: Jun. 4, 2024

(54) METHOD FOR STIMULATING RETINAL CELLS AND TREATING VISION LOSS

(71) Applicant: LambdaVision Incorporated, Farmington, CT (US)

(72) Inventors: Robert R Birge, Peyton, CO (US); Nicole Wagner, Ashford, CT (US); Jordan A Greco, Rocky Hill, CT (US)

(73) Assignee: LambdaVision Incorporated, Farmington, CT (US)

( * ) Notice: Subject to any disclaimer, the term of this patent is extended or adjusted under 35 U.S.C. 154(b) by 1247 days.

(21) Appl. No.: 16/611,095

(22) PCT Filed: May 8, 2018

(86) PCT No.: PCT/US2018/031469
§ 371 (c)(1),
(2) Date: Nov. 5, 2019

(87) PCT Pub. No.: WO2018/208703
PCT Pub. Date: Nov. 15, 2018

(65) Prior Publication Data
US 2020/0054441 A1 Feb. 20, 2020

Related U.S. Application Data

(60) Provisional application No. 62/502,815, filed on May 8, 2017.

(51) Int. Cl.
| | |
|---|---|
| *A61F 2/14* | (2006.01) |
| *A61F 9/00* | (2006.01) |
| *A61K 38/16* | (2006.01) |
| *A61L 27/22* | (2006.01) |
| *A61N 1/36* | (2006.01) |

(Continued)

(52) U.S. Cl.
CPC .............. *A61F 2/14* (2013.01); *A61F 9/0017* (2013.01); *A61K 38/164* (2013.01); *A61L 27/227* (2013.01); *A61N 1/36046* (2013.01); *A61N 5/0603* (2013.01); *A61N 5/0622* (2013.01); *B29D 11/0073* (2013.01); *B32B 7/023* (2019.01); *A61F 2009/00863* (2013.01); *A61L 2300/252* (2013.01); *A61L 2430/16* (2013.01); *A61N 2005/0648* (2013.01); *A61N 2005/0663* (2013.01); *B32B 2535/00* (2013.01)

(58) Field of Classification Search
None
See application file for complete search history.

(56) References Cited

U.S. PATENT DOCUMENTS 7,573,024 B2   8/2009 Knopf et al.
8,563,026 B2  10/2013 Birge et al.
(Continued)

OTHER PUBLICATIONS

Supplementary European Search Report, EP 18797877 corresponding to PCT/US2018/031469, mailed Jan. 19, 2021, 8 pages.
(Continued)

*Primary Examiner* — David H Willse
(74) *Attorney, Agent, or Firm* — Wiggin and Dana LLP

(57) ABSTRACT

Protein-based subretinal implants offer a new approach to restoring vision for patients blinded by conditions such as age-related macular degeneration (AMD) and retinitis pigmentosa (RP). The present invention relates to bacteriorhodopsin-based (BR-based) retinal implants that can be implanted in a subretinal position to replace degenerated photoreceptor cells.

46 Claims, 15 Drawing Sheets

(51) Int. Cl.
     A61N 5/06    (2006.01)
     B29D 11/00   (2006.01)
     B32B 7/023   (2019.01)
     A61F 9/008   (2006.01)

(56) References Cited

U.S. PATENT DOCUMENTS

| | | |
|---|---|---|
| 8,883,719 B2 | 11/2014 | Birge et al. |
| 9,023,989 B2 | 5/2015 | Birge et al. |
| 2006/0009805 A1 | 1/2006 | Jensen et al. |
| 2009/0229669 A1 | 9/2009 | Birge et al. |
| 2009/0268511 A1 | 10/2009 | Birge et al. |
| 2010/0226957 A1 | 9/2010 | Birge et al. |

OTHER PUBLICATIONS

Wagner, N.L. et al., "Chapter 9: Visual Restoration using Microbial Rhodopsins", Bionanotechnology: Biological Self-Assembly and its Applications; (2013) pp. 205-240, Caister Academic Press, Norfolk, UK.

Greco, J.A. et al., "Pixel Characterization of a Protein-Based Retinal Implant Using a Microfabricated Sensor Array", International Journal of High Speed Electronics and Systems; (2017) pp. 1740012-(1-20).

Chen, Z. et al., "Protein-based Artificial Retinas", Tibtech; (1993) pp. 292-300.

He, J. et al., "Oriented Bacteriorhodopsin/Polycation Multilayers by Electrostatic Layer-by-Layer Assembly", Langmuir; (1998) pp. 1674-1679.

Lilley, S. et al., "The Discovery and Characterization of a Proton-Gated Sodium Current in Rat Retinal Ganglion Cells", The Journal of Neuroscience; (2004) pp. 1013-1022.

Lilley, S. et al., "Characterisation of a Novel Proton-Gated Sodium Current in Rat Retinal Ganglion Cells", Journal of Physiology; (2001) pp. 83-84.

Birge, R. et al., "Biomolecular Electronics: Protein-Based Associative Processors and Volumetric Memories", Journal of Physical Chemistry B; (1999) pp. 10746-10766.

Jensen, R.J. et al., :Effects of GABA Receptor Antagonists on Thresholds of P23H Rat Retinal Ganglion Cells to Electrical Stimulation of the Retina, Journal of Neural Engineering; (2011) pp. 035002(1-8).

International Search Report, PCT/US2018/031469, Mailed May 8, 2018.

Greco, J., et al., "Activation of retinal ganglion cells using a biomimetic artificial retina", Journal of Neural Engineering; 18 (2021) 066027.

000
METHOD FOR STIMULATING RETINAL CELLS AND TREATING VISION LOSS

STATEMENT REGARDING FEDERALLY SPONSORED RESEARCH

This invention was made with government support under grants from the National Institutes of Health (GM-34548, 1R41 EY023461-01) and the National Science Foundation (IIP-1448244, IIP-1632465). The government has certain rights in the invention.

FIELD OF THE INVENTION

Protein-based subretinal implants offer a new approach to restoring vision for patients blinded by conditions such as age-related macular degeneration (AMD) and retinitis pigmentosa (RP). The present invention relates to bacteriorhodopsin-based (BR-based) retinal implants that can be implanted in a subretinal position to replace degenerated photoreceptor cells.

BACKGROUND OF THE INVENTION

The retina is a multilayered tissue that lines the concave inner surface of the back of the eye. Photoreceptor cells within the retina are activated by light that enters the eye and converts the light signals into electrochemical signals that are conveyed to retinal neurons. The retinal neurons, in turn, relay the signals to the visual centers of the brain via the optic nerve, thereby allowing the brain to perceive visual images. Photoreceptor cells are broadly categorized as rod cells and cone cells, which are named for their shape. Whereas cone cells contain photopigments that are necessary for color vision, rod cells contain a photopigment, rhodopsin, that is highly sensitive to light and thus allows vision under dim light conditions, e.g., night conditions. A rod cell is sensitive enough to become activated by a single photon of light, whereas a cone cell requires tens to hundreds of photons to become activated.

Rhodopsin, the photoreceptive pigment of rod cells, undergoes a conformational change when activated by a photon of light. Rhodopsin consists of a seven-pass transmembrane protein called opsin that is covalently bound to a prosthetic group called retinal, a derivative of vitamin A. Non-activated retinal exists in the 11-cis form, whereas stimulation by light induces a conformational change to the all-trans form. The conformational change in retinal induces a corresponding conformational change in the covalently bound opsin polypeptide, thereby triggering a second messenger cascade within the photoreceptor cell that results in the transmission of signals to the appropriate retinal neurons. These signals are transmitted along the optic nerve to the visual centers of the brain, which allows the brain to process the visual input and perceive a visual image.

Various diseases and conditions that destroy photoreceptor cells of the retina cause partial or full vision loss. Two major diseases of the retina are age-related macular degeneration (AMD) and retinitis pigmentosa (RP). As the leading cause of vision loss and blindness in older adults, AMD causes both rod and cone photoreceptor cells, located within the macula at the center of the retina, to deteriorate. Furthermore, AMD affects central vision and thus causes difficulty with reading, driving, and other tasks that require high-contrast vision.

The other disease, RP, is an inherited condition in which the rod photoreceptor cells degenerate, thereby causing vision loss and blindness. The loss of rod cells impairs the ability to see in dim light and gradually reduces peripheral vision until the patient suffers from tunnel vision and, ultimately, blindness.

To date, a number of artificial retina prototypes have been investigated for the treatment of such retinal diseases and conditions, but each has distinct disadvantages. One of the most promising designs is an epiretinal implant, the Argus II, designed by researchers at the University of Southern California and commercialized by Second Sight. The prosthetic employs the use of an external camera, mounted on a pair of glasses, connected to a microelectrode array by a connecting cable. The electrode array provides electrical stimulation directly to the ganglion cells. In clinical trials, subjects were able to perceive light using an 8×8 electrode array, and were able to detect motion, and recognize simple shapes. However, this design has a distinct disadvantage in that it requires external hardware, such as glasses and a surgically implanted external device. Moreover, the prosthetic provides low resolution that is insufficient for restoring functional vision, and the complexity of the surgical procedures required for implantation limit adoptability from the retinal surgeon community.

What is needed are high-resolution retinal implants that are less surgically invasive, which can at least partially restore quality vision to patients suffering from vision loss resulting from the loss of photoreceptor cells, as a consequence of retinal disease or damage.

It is apparent from the foregoing there is an ongoing need for developing safe and effective methods for treating vision loss.

SUMMARY OF THE INVENTION

The protein-based subretinal implants of the present invention offer a new approach to restoring vision for patients blinded by AMD and RP. Ex vivo extracellular recording experiments with P23H transgenic rats were employed to demonstrate the ability of such an ion-mediated, protein-based prosthetic to stimulate the bipolar and ganglion cells of a degenerated retina.

The present invention provides an implant capable of performing at high resolution and that can be activated by light conditions similar to indoor ambient lighting, such as high pixel resolution methods for stimulating retinal cells and treating vision loss.

BRIEF DESCRIPTION OF THE DRAWINGS

FIG. 4A demonstrates that the retinal implant with high optical density (OD) is capable of stimulating the retinal tissue with high efficiency when oriented such that protons are pumped towards the retina (the traces with closed squares and triangles, upper trace in FIG. 4A, lower trace in FIG. 4B). If an implant with lower OD is used (the traces with open squares and triangles, lower trace in FIG. 4A, upper trace in FIG. 4B), the efficiency is significantly decreased. When the implant orientation is reversed so that protons are pumped away from the retina, FIG. 4B, there is little to no activity measured. The square and triangular data points refer to measured actions potentials with positive and negative amplitude, respectively. All data uses a 30 µV threshold for analysis.

FIGS. 5A, 5C, and 5E correspond to the case in which the implant is oriented to pump protons towards neural tissue ([$H^+$] increase). FIGS. 5B, 5D, and 5F are for the control, in which the implant was placed in the opposite orientation ([$H^+$] decrease). The y-axis is adjusted so that it is the average number of observations per 100 sweeps. Incident light (630 nm, 1 ms pulse) intensity increases from top to bottom (5A/5B: 20.5 mW/cm$^2$; 5C/5D: 29.5 mW/cm$^2$; 5E/5F: 49.89 mW/cm$^2$).

FIG. 7B) with the output from a projector light with either a green or red interference filter employed. The coupling efficiencies of the light source with the spectra are indicated on the right-hand side of the plots. It is seen that the red interference filter couples with the bR absorption spectrum, but with much lower efficiency to rat green cone pigment.

FIG. 8A, FIG. 8B, and FIG. 8C correspond to selected activation of electrodes E3, E4, and E5, respectively. The upper plot in each panel illustrates the percent signal rate for each electrode following illumination, and each plot is normalized to the maximum. The lower plot in each panel shows the location and relative beam spot size.

DETAILED DESCRIPTION OF THE INVENTION

Figure 1:
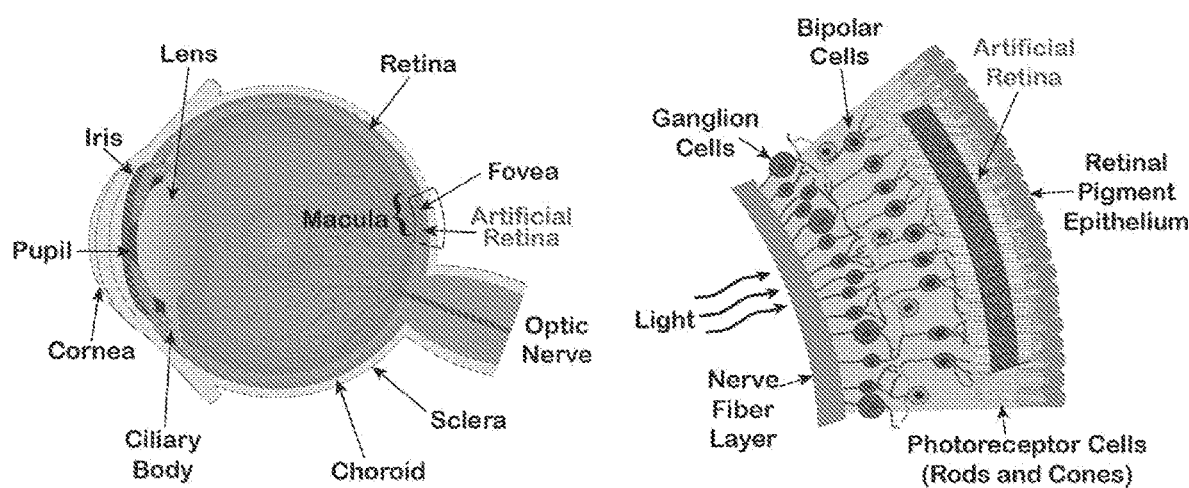
FIG. 1 shows the application of the protein-based retinal implant. Retinal degenerative diseases, including AMD and RP, are characterized by the loss of the photoreceptor cells within the retina. Individuals that are affected by these diseases lose vision and ultimately will go blind. The bacteriorhodopsin-based (BR-based) retinal implant replaces the degenerated photoreceptor cells and is placed in a subretinal position. Upon the absorption of light, the implant generates an ion gradient that stimulates the remaining retinal tissue. See, Wagner, N. L. et al. In Bionanotechnology: Biological Self-Assembly and its Applications; B. A. Rehm, ed. Caister Academic Press, Norfolk, UK 2013, 205-240; Greco, J. A. et al. *Int. J. High Speed Electron. Syst.* 2017, 26, 1740012-1-17400120-20; and Chen, Z.; Birge, R. R. *Trends Biotech.* 1993, 11, 292-300.

The present invention relates to a method for treating a patient having loss of vision caused by loss of retinal cells, comprising,
(a) implanting into an eye of the patient a bacteriorhodopsin-based retinal implant, and
(b) activating the implant with a light source,
wherein the implant stimulates retinal cells such that the stimulation is provided at a resolution with pixel dimensions less than about 500 µm, or less than about 350 µm, or less than about 250 µm, or less than about 200 µm, or less than about 150 µm, or less than about 100 µm, or less than about 75 µm, or less than about 50 µm, or less than about 40 µm, or less than about 30 µm, or less than about 25 µm.

In another aspect, the present invention relates to a method for treating a patient having loss of vision caused by loss of retinal cells, comprising,
(a) implanting into an eye of the patient a bacteriorhodopsin-based retinal implant, and
(b) activating the implant with a light source,
wherein the implant stimulates retinal cells such that the stimulation is provided at a resolution limited by (i) the diffraction limit of the light source or (ii) when the retinal implant further comprises an ion-permeable substrate (scaffold), the aperture diameter and density of the ion-permeable substrate (scaffold).

In another aspect, the present invention relates to a method for treating a patient having loss of vision caused by loss of retinal cells, comprising,
(a) implanting into an eye of the patient a bacteriorhodopsin-based retinal implant, and
(b) activating the implant with a light source,
wherein the implant stimulates retinal cells such that the stimulation is provided at a resolution with a pixel density of about 4 pixels/mm$^2$ and pixel dimension of about 500 µm, or with a pixel density of about 8 pixels/mm$^2$ and pixel diameter of about 350 µm, or with a pixel density of about 16 pixels/mm$^2$ and pixel diameter of about 250 µm, or with a pixel density of about 25 pixels/mm$^2$ and pixel diameter of about 200 µm, or with a pixel density of about 44 pixels/mm$^2$ and pixel diameter of about 150 µm, or with a pixel density of about 100 pixels/mm$^2$ and pixel diameter of about 100 µm, or with a pixel density of about 178 pixels/mm$^2$ and pixel diameter of about 75 µm, or with a pixel density of about 400 pixels/mm$^2$ and pixel diameter of about 50 µm, or with a pixel density of about 625 pixels/mm$^2$ and pixel diameter of about 40 µm, or with a pixel density of about 1111 pixels/mm$^2$ and pixel diameter of about 30 µm, or with a pixel density of about 1600 pixels/mm$^2$ and pixel diameter of about 25 µm.

In another aspect, the present invention relates to a method wherein the bacteriorhodopsin-based retinal implant, comprises at least one substrate layer (scaffold) and a bacteriorhodopsin film, wherein the bacteriorhodopsin film comprises a plurality of individual layers of a native bacteriorhodopsin or a bacteriorhodopsin mutant, wherein each individual layer of the native bacteriorhodopsin or bacteriorhodopsin mutant alternates with a layer of a cationic polymer, and wherein the bacteriorhodopsin mutant is selected from the group consisting of a chloride pump mutant, a dipole mutant, a photocycle mutant, a gold-binding mutant, an ion pump mutant, a Q-state mutant, and combinations thereof, and In another aspect, the present invention relates to a method wherein the light source is a light source emitting human visible wavelengths, i.e. about 400 to about 700 nm.

In another aspect, the present invention relates to a method wherein the light source has an intensity (power density) less than about 100 mW/cm$^2$, 50 mW/cm$^2$, 40 mW/cm$^2$, or less than about 30 mW/cm$^2$, or less than about 20 mW/cm$^2$, or less than about 10 mW/cm$^2$, or less than about 5 mW/cm$^2$, or less than about 1 mW/cm$^2$.

In another aspect, the present invention relates to a method wherein the light source is a pulsed light source.

In another aspect, the present invention relates to a method wherein the light source is a continuous light source.

In another aspect, the present invention relates to a method wherein the implant is a biocompatible, ion permeable retinal implant.

In another aspect, the present invention relates to a method wherein in the implant is made using layer-by-layer assembly.

In another aspect, the present invention relates to a method wherein the implant is implanted in a position selected from a subretinal position or an epiretinal position.

In another aspect, the present invention relates to a method wherein the implant is implanted in a subretinal position.

In another aspect, the present invention relates to a method wherein the implant is implanted in an epiretinal position.

In another aspect, the present invention relates to a method wherein the retinal cells are selected from retinal ganglion cells, retinal bipolar cells, retinal photoreceptor cells, and combinations thereof.

In another aspect, the present invention relates to a method wherein the retinal cells are selected from retinal ganglion cells.

In another aspect, the present invention relates to a method wherein the retinal cells are selected from retinal bipolar cells.

In another aspect, the present invention relates to a method wherein the retinal cells are selected from retinal photoreceptor cells.

In another aspect, the present invention relates to a method wherein the retinal implant comprises at least about 100 layers of a native bacteriorhodopsin or a bacteriorhodopsin mutant, or at least about 150 layers of a native bacteriorhodopsin or a bacteriorhodopsin mutant, or at least about 200 layers of a native bacteriorhodopsin or a bacteriorhodopsin mutant.

In another aspect, the present invention relates to a method wherein the retinal implant further provides a temporal resolution of at least about 30 milliseconds.

In another aspect, the present invention relates to a method wherein the retinal implant further provides a temporal resolution of at least about 20 milliseconds.

In another aspect, the present invention relates to a method wherein the retinal implant further provides a temporal resolution of at least about 10 milliseconds.

In another aspect, the present invention relates to a method wherein the retinal implant initiates (provides) to the cells an action potential of about 40 µV.

In another aspect, the present invention relates to a method wherein the retinal implant initiates (provides) to the cells an action potential of about 30 µV.

In another aspect, the present invention relates to a method wherein the retinal implant initiates (provides) to the cells an action potential of about 20 µV.

In another aspect, the present invention relates to a method wherein the retinal implant provides a unidirectional proton gradient.

In another aspect, the present invention relates to a method wherein the unidirectional proton gradient is directed to the retinal cells, wherein the retinal cells are selected from retinal ganglion cells or retinal bipolar cells.

In another aspect, the present invention relates to a method wherein the implant is implanted in a position selected from a subretinal position or an epiretinal position.

In another aspect, the present invention relates to a method wherein the bacteriorhodopsin-based retinal implant comprises bacteriorhodopsin molecules such that they are uniformly (homogeneously) oriented.

In another aspect, the present invention relates to a method wherein the retinal implant is used at or below physiological temperature (~37° C.).

In another aspect, the present invention relates to a method wherein the retinal implant is used at physiological pH (about 7.0 to about 7.2).

In another aspect, the present invention relates to a method wherein the vision loss is caused by loss of retinal photoreceptor cells.

In another aspect, the present invention relates to a method wherein the substrate layer is an ion permeable layer and is on one or both sides of the implant.

In another aspect, the present invention relates to a method wherein the substrate layer is selected from polyethylene terephthalate (PET), 2-hydroxyethyl methacrylate (HEMA), 2-phenylethyl methacrylate (PEM), polyethylene glycol (PEG), methyl methacrylate (MMA), polydimethylsiloxane (PDMS) macromer, poly(vinyl pyrrolidone) (PVP), poly(p-xylylene) (also known as parylene), polyvinyl alcohol (PVA) hydrogel, and combinations thereof.

In another aspect, the present invention relates to a method wherein the substrate layer (scaffold) is less than 100 µm in thickness and contains an evenly distributed array of apertures of a diameter less than about 100 µm.

In another aspect, the present invention relates to a method wherein the bacteriorhodopsin-based retinal implant is based on native bacteriorhodopsin.

In another aspect, the present invention relates to a method wherein the bacteriorhodopsin-based retinal implant is based on a bacteriorhodopsin mutant In another aspect, the present invention relates to a method wherein the mutant is a Q-state mutant.

In another aspect, the present invention relates to a method wherein the mutant has been optimized to have a high dipole moment.

In another aspect, the present invention relates to a method wherein the mutant has been optimized for efficient Q-state formation.

In another aspect, the present invention relates to a method for stimulating retinal cells comprising,
(a) contacting the retinal cells with a bacteriorhodopsin-based retinal implant,
(b) activating the implant with a light source,
wherein
(i) wherein the implant stimulates retinal cells such that the stimulation is provided at a resolution with pixel dimensions less than about 500 µm, or less than about 350 µm, or less than about 250 µm, or less than about 200 µm, or less than about 150 µm, or less than about 100 µm, or less than about 75 µm, or less than about 50

μm, or less than about 40 μm, or less than about 30 μm, or less than about 25 μm; or (ii) wherein the implant stimulates retinal cells such that the stimulation is provided at a resolution limited by (i) the diffraction limit of the light source or (ii) when the retinal implant further comprises an ion-permeable substrate (scaffold), the aperture diameter and density of the ion-permeable substrate (scaffold); or (iii) wherein the implant stimulates retinal cells such that the stimulation is provided at a resolution with a pixel density of about 4 pixels/mm$^2$ and pixel dimension of about 500 μm, or with a pixel density of about 8 pixels/mm$^2$ and pixel diameter of about 350 μm, or with a pixel density of about 16 pixels/mm$^2$ and pixel diameter of about 250 μm, or with a pixel density of about 25 pixels/mm$^2$ and pixel diameter of about 200 μm, or with a pixel density of about 44 pixels/mm$^2$ and pixel diameter of about 150 μm, or with a pixel density of about 100 pixels/mm$^2$ and pixel diameter of about 100 μm, or with a pixel density of about 178 pixels/mm$^2$ and pixel diameter of about 75 μm, or with a pixel density of about 400 pixels/mm$^2$ and pixel diameter of about 50 μm, or with a pixel density of about 625 pixels/mm$^2$ and pixel diameter of about 40 μm, or with a pixel density of about 1111 pixels/mm$^2$ and pixel diameter of about 30 μm, or with a pixel density of about 1600 pixels/mm$^2$ and pixel diameter of about 25 μm.

In another aspect, the present invention relates to a retinal implant for treating a patient having loss of vision caused by loss of retinal cells, comprising, a retinal implant that stimulates retinal cells such that the stimulation is provided at a resolution with pixel dimensions less than about 500 μm, or less than about 350 μm, or less than about 250 μm, or less than about 200 μm, or less than about 150 μm, or less than about 100 μm, or less than about 75 μm, or less than about 50 μm, or less than about 40 μm, or less than about 30 μm, or less than about 25 μm.

In another aspect, the present invention relates to a retinal implant for treating a patient having loss of vision caused by loss of retinal cells, comprising, a retinal implant that stimulates retinal cells such that the stimulation is provided at a resolution limited by (i) the diffraction limit of the light source or (ii) when the retinal implant further comprises an ion-permeable substrate (scaffold), the aperture diameter and density of the ion-permeable substrate (scaffold).

In another aspect, the present invention relates to a retinal implant for treating a patient having loss of vision caused by loss of retinal cells, comprising, retinal implant that stimulates retinal cells such that the stimulation is provided at a resolution with a pixel density of about 4 pixels/mm$^2$ and pixel dimension of about 500 μm, or with a pixel density of about 8 pixels/mm$^2$ and pixel diameter of about 350 μm, or with a pixel density of about 16 pixels/mm$^2$ and pixel diameter of about 250 μm, or with a pixel density of about 25 pixels/mm$^2$ and pixel diameter of about 200 μm, or with a pixel density of about 44 pixels/mm$^2$ and pixel diameter of about 150 μm, or with a pixel density of about 100 pixels/mm$^2$ and pixel diameter of about 100 μm, or with a pixel density of about 178 pixels/mm$^2$ and pixel diameter of about 75 μm, or with a pixel density of about 400 pixels/mm$^2$ and pixel diameter of about 50 μm, or with a pixel density of about 625 pixels/mm$^2$ and pixel diameter of about 40 μm, or with a pixel density of about 1111 pixels/mm$^2$ and pixel diameter of about 30 μm, or with a pixel density of about 1600 pixels/mm$^2$ and pixel diameter of about 25 μm.

In another aspect, the present invention relates to a retinal implant wherein the bacteriorhodopsin-based retinal implant, comprises at least one substrate layer (scaffold) and a bacteriorhodopsin film, wherein the bacteriorhodopsin film comprises a plurality of individual layers of a native bacteriorhodopsin or a bacteriorhodopsin mutant, wherein each individual layer of the native bacteriorhodopsin or bacteriorhodopsin mutant alternates with a layer of a cationic polymer, and wherein the bacteriorhodopsin mutant is selected from the group consisting of a chloride pump mutant, a dipole mutant, a photocycle mutant, a gold-binding mutant, an ion pump mutant, a Q-state mutant, and combinations thereof, and In another aspect, the present invention relates to a retinal implant wherein the light source is a light source emitting human visible wavelengths, i.e. about 400 to about 700 nm.

In another aspect, the present invention relates to a retinal implant wherein the light source has an intensity (power density) less than about 100 mW/cm$^2$, 50 mW/cm$^2$, 40 mW/cm$^2$, or less than about 30 mW/cm$^2$, or less than about 20 mW/cm$^2$, or less than about 10 mW/cm$^2$, or less than about 5 mW/cm$^2$, or less than about 1 mW/cm$^2$.

In another aspect, the present invention relates to a retinal implant wherein the light source is a pulsed light source.

In another aspect, the present invention relates to a retinal implant wherein the light source is a continuous light source.

In another aspect, the present invention relates to a retinal implant wherein the implant is a biocompatible, ion permeable retinal implant.

In another aspect, the present invention relates to a retinal implant wherein the implant is made using layer-by-layer assembly.

In another aspect, the present invention relates to a retinal implant wherein the implant is implanted in a position selected from a subretinal position or an epiretinal position.

In another aspect, the present invention relates to a retinal implant wherein the implant is implanted in a subretinal position.

In another aspect, the present invention relates to a retinal implant wherein the implant is implanted in an epiretinal position.

In another aspect, the present invention relates to a retinal implant wherein the retinal cells are selected from retinal ganglion cells, retinal bipolar cells, retinal photoreceptor cells, and combinations thereof.

In another aspect, the present invention relates to a retinal implant wherein the retinal cells are selected from retinal ganglion cells.

In another aspect, the present invention relates to a retinal implant wherein the retinal cells are selected from retinal bipolar cells.

In another aspect, the present invention relates to a retinal implant wherein the retinal cells are selected from retinal photoreceptor cells.

In another aspect, the present invention relates to a retinal implant wherein the retinal implant comprises at least about 100 layers of a native bacteriorhodopsin or a bacteriorhodopsin mutant, or at least about 150 layers of a native bacteriorhodopsin or a bacteriorhodopsin mutant, or at least about 200 layers of a native bacteriorhodopsin or a bacteriorhodopsin mutant.

In another aspect, the present invention relates to a retinal implant wherein the retinal implant further provides a temporal resolution of at least about 30 milliseconds.

In another aspect, the present invention relates to a retinal implant wherein the retinal implant further provides a temporal resolution of at least about 20 milliseconds.

In another aspect, the present invention relates to a retinal implant wherein the retinal implant further provides a temporal resolution of at least about 10 milliseconds.

In another aspect, the present invention relates to a retinal implant wherein the retinal implant initiates (provides) to the cells an action potential of about 40 μV.

In another aspect, the present invention relates to a retinal implant wherein the retinal implant initiates (provides) to the cells an action potential of about 30 μV.

In another aspect, the present invention relates to a retinal implant wherein the retinal implant initiates (provides) to the cells an action potential of about 20 μV.

In another aspect, the present invention relates to a retinal implant wherein the retinal implant provides a unidirectional proton gradient.

In another aspect, the present invention relates to a retinal implant wherein the unidirectional proton gradient is directed to the retinal cells, wherein the retinal cells are selected from retinal ganglion cells or retinal bipolar cells.

In another aspect, the present invention relates to a retinal implant wherein the implant is implanted in a position selected from a subretinal position or an epiretinal position.

In another aspect, the present invention relates to a retinal implant wherein the bacteriorhodopsin-based retinal implant comprises bacteriorhodopsin molecules such that they are uniformly (homogeneously) oriented.

In another aspect, the present invention relates to a retinal implant wherein the retinal implant is used at or below physiological temperature (~37° C.).

In another aspect, the present invention relates to a retinal implant wherein the retinal implant is used at physiological pH (about 7.0 to about 7.2).

In another aspect, the present invention relates to a retinal implant wherein the vision loss is caused by loss of retinal photoreceptor cells.

In another aspect, the present invention relates to a retinal implant wherein the substrate layer is an ion permeable layer and is on one or both sides of the implant.

In another aspect, the present invention relates to a retinal implant wherein the substrate layer is selected from polyethylene terephthalate (PET), 2-hydroxyethyl methacrylate (HEMA), 2-phenylethyl methacrylate (PEM), polyethylene glycol (PEG), methyl methacrylate (MMA), polydimethylsiloxane (PDMS) macromer, poly(vinyl pyrrolidone) (PVP), poly(p-xylylene) (also known as parylene), polyvinyl alcohol (PVA) hydrogel, and combinations thereof.

In another aspect, the present invention relates to a retinal implant wherein the substrate layer (scaffold) is less than 100 μm in thickness and contains an evenly distributed array of apertures of a diameter less than about 100 μm.

In another aspect, the present invention relates to a retinal implant wherein the bacteriorhodopsin-based retinal implant is based on native bacteriorhodopsin.

In another aspect, the present invention relates to a retinal implant wherein the bacteriorhodopsin-based retinal implant is based on a bacteriorhodopsin mutant In another aspect, the present invention relates to a retinal implant wherein the mutant is a Q-state mutant.

In another aspect, the present invention relates to a retinal implant wherein the mutant has been optimized to have a high dipole moment.

In another aspect, the present invention relates to a retinal implant wherein the mutant has been optimized for efficient Q-state formation.

These and other aspects of the present invention will become apparent from the disclosure herein.

Bacteriorhodopsin-Based Retinal Implants:

The retinal implants of the present invention (FIG. 1) use a light-activated protein, bateriorhodopsin (BR), as the photoactive medium to both absorb incident light and initiate a proton motive force to activate the remaining neural circuitry of a degenerated retina to stimulate a visual response. See, Birge, R. R.; Nollenberger, M. Ranaghan, M. J.; Sandberg, D. J.; Wagner, Nicole L. Protein-Based Artificial Retinas U.S. Pat. No. 8,563,026; and Chen, Z.; Birge, R. R., Protein Based Artificial Retinas. *Trends Biotech.* 1993, 11, 292-300. Bacteriorhodopsin is an excellent candidate for this application because the proton-pumping function of the protein operates at a high quantum efficiency (65%) that is identical to the native visual pigment, rhodopsin. The protein also functions under high temperatures (>80°) C., high light intensities, and highly saline environments. The architecture of the retinal implant allows for an optical density of the protein capable of absorbing sufficient incident light to generate an ion-gradient for retinal stimulation. This performance feature is facilitated by a layer-by-layer (LBL) electrostatic adsorption approach that is used to generate highly uniform films. The result is a film that can create a unidirectional proton gradient. An automated LBL system was developed for this bottom-up manufacturing method to generate the multilayer implants. The high optical density of the retinal implant circumvents inherent issues of expression levels with gene therapy and optogenetic approaches, which seek to express similar photoactive proteins for light-capture in degenerated retinas. Ex vivo extracellular recording experiments with P23H transgenic rats are employed to demonstrate the ability of these ion-mediated, protein-based prosthetics to stimulate the bipolar and ganglion cells of a degenerated retina.

The molecular packing of the BR protein within the layers of the retinal implant constructs results in a high pixel density, which leads to spatial resolution that is only limited by diffusion rates and the lateral diffusion of protons through the ion-permeable scaffold. Importantly, the retinal implant is powered by incident light, which is an advantage compared to other electronic type implants which require external cables, electrodes, or power supplies. Thus, the retinal implant of the present invention is surgically less invasive, which greatly reduces the time required for implantation, as well as the chance of infection due to mechanical fixation. The implant will also allow for patients to use natural eye movements to scan the visual scene, and provide normal visual perception without delays in signal transmission.

Figure 2:
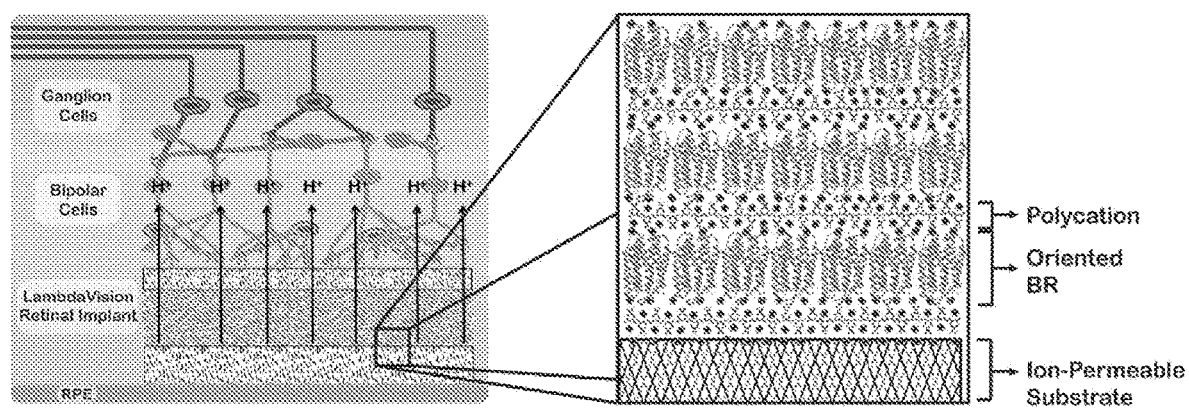
FIG. 2 shows a schematic of the retinal implant and a diagram showing the arrangement of alternating layers of BR and polycation. See, He, J. A. et al. *Langmuir* 1998, 14, 1674-1679. The protein-based retinal implant is based on electrostatic interactions between an ion-permeable membrane, a polycation, and BR. The resulting multi-layer film generates a unidirectional ion gradient that is used to stimulate the degenerated retinal tissue.

Construction and Design of Multilayer Thin Films:

The BR-based, retinal implants of the present invention (FIG. 2) are comprised of a multilayered BR thin film generated via sequential LBL electrostatic adsorption using a custom-made LBL dipping machine. The LBL deposition of BR uses a commercially available, ion-permeable microfiber, known as Dacron®, as the scaffolding in the retinal implant. Dacron® has found successful application in the eye and can be used to attach and orient the protein directly on the surface. In order to harness the ability of BR to generate a sufficient pH gradient for retinal stimulation, the protein is uniformly oriented across the Dacron® surface area at an optimal density, and contains enough layers of BR to adequately absorb incident light while also generating a pH gradient. Furthermore, we have found that it is useful to provide a scaffold with appropriate size spacings, as described below.

Stability and Biocompatibility of the Retinal Implant:

The long-term stability of BR to thermal and photochemical degradation is well documented in the literature. The protein can withstand temperatures greater than 80° C., which far exceeds that of normal human body temperature. Moreover, the cyclicity of the protein (i.e., the number of times that the protein can be photochemically cycled before the sample degrades by 1/e) is roughly $10^6$. This value is considerably greater than most synthetic photochromic materials. This stability is achieved through the isolation of the protein within a two-dimensional crystalline lattice of trimers (purple membrane) surrounded by the native lipid membrane. The LBL-assembled retinal implants are held together by efficient electrostatic interactions, which bind BR to the polycation.

Overview of the Mechanism of Action:

Microbial rhodopsins serve as potential optogenetic tools for treating inherited retinal disorders. Optogenetics approaches use light-activated proteins, including channelrhodopsin-2 (ChR-2) and halorhodopsin (HR), expressed in AAVs that are directed toward bipolar and ganglion cells to replace the photosensitivity of the degenerated photoreceptor cells. These therapies exploit the fact that the neural network remains largely intact for both RP and AMD, despite the loss of photoreceptor cells. Theoretical models have been used to show that altering the ionic concentration of $Na^+$, $K^+$, and $Cl^-$ ions surrounding retinal cells can trigger a nerve impulse, and light-activated ion channels and pumps such as ChR-2 ($Na^+/K^+$ channel) and HR ($Cl^-$ pump) can be used to depolarize and hyperpolarize these neural cells, respectively. Retinal ganglion cells (RGCs) contain proton-gated analogues of epithelial $Na^+$ channels embedded in the neural cell membrane. Consequently, proton pumps such as BR have also been considered as optogenetic tools to restore vision to patients with retinal degeneration. Lilley et al. measured the threshold of proton-induced retinal stimulation (~pH 6.5) and reproducibly demonstrated that rapid millisecond pulses of extracellular acidification evokes the normal pattern of electrical activity of RGCs. See, Lilley, S.; LeTissier, P.; Robbins, J., The Discovery and Characterization of a Proton-Gated Sodium Current in Rat Retinal Ganglion Cells. *J. Neurosci.* 2004, 24, 1013-1022; Lilley, S.; Robbins, J., Characterisation of a Novel Proton-Gated Sodium Current in Rat Retinal Ganglion Cells. *J. Physiol.* 2001, 531, 83P-84P. The ~10 ms duration of the BR photocycle and the ability to modulate localized acidity makes BR another viable candidate for ion-mediated stimulation of the retina. The present invention utilizes this principle by creating a stable, biocompatible implantable prosthetic that functions at the same efficiency as the native pigments in the photoreceptor cells.

The BR-based retinal implant of the present invention employs some of the same principles of the ion-mediated optogenetic therapies, however, there are some key advantages to the prosthetic that overcome inherent drawbacks of gene therapy approaches. First, the RPE65 gene mutation that has been primarily targeted by optogenetic therapies affects only about 6,000 individuals worldwide, whereas the present invention has the potential to treat the global 1.5 million RP population affected by various genetic mutations. In addition, optogenetic tools such as ChR-2 have $\lambda_{max}$ values that are on the blue edge of the visible spectrum (~470 nm), while BR has a broad $\lambda_{max}$ at 570 nm that spans much of the central portion of the visible spectrum. This feature offers greater sensitivity, while also removing the need for relying on shorter wavelengths that border the UV region of the spectrum. Lastly, the expression levels of the non-native ChR-2 and HR proteins can be limited and unstable, which leads to the need for dangerous, high-intensity light sources to activate the targeted neural cells. The multilayered protein-based retinal prosthetic circumvents this issue by using hundreds of layers of BR, which require lower light intensities to generate a sufficient ion gradient.

Pixel Mediation Using Q-State Mutants:

In addition to the photochemistry that defines the proton-pumping mechanism of the light-activated protein, BR has access to a branched photocycle via a sequential two-photon process. The Q-state contains a 9-cis retinal chromophore (as opposed to all-trans in the BR resting state), which is hydrolyzed from the protein and leads to an isolated, blue-shifted photoproduct that is stable on the order of several years at ambient temperature. See, Birge, R. R.; Gillespie, N. B.; Izaguirre, E. W.; Kusnetzow, A.; Lawrence, A. F.; Singh, D.; Song, Q. W.; Schmidt, E.; Stuart, J. A.; Seetharaman, S., et al., Biomolecular Electronics: Protein-Based Associative Processors and Volumetric Memories. *J. Phys. Chem. B* 1999, 103, 10746-10766. The Q-state prevents the protein from undergoing the light-induced photocycle, which offers a means to convert active pixels in a protein-based retinal implant to inactive pixels. This feature could be advantageous for modulating the pixel density of the implants and deactivating specific areas to prevent interference with photoreceptor cells, either prior to or following surgical implantation. The native, wild-type protein cannot efficiently access this photoproduct, and various mutants of BR have been identified that provide greater access and stability of the Q-state. Birge, R. R.; Rangarajan, R.; McCleary, K. N. Bacteriorhodopsin protein variants and methods of use for long term data storage. U.S. Pat. No. 8,883,719. The retinal implants described in this invention can be manufactured identically using the wild-type form of the protein or using a Q-state mutant, and the function and methods of stimulation described in the invention herein can be modulated based on this unique photochemistry.

Examples

The following examples further describe and demonstrate embodiments within the scope of the present invention. The Examples are given solely for purpose of illustration and are not to be construed as limitations of the present invention, as many variations thereof are possible without departing from the spirit and scope of the invention.

Ex Vivo Study Design:

The evaluation of the protein-based retinal implants of the present invention was focused on quantifying the spatial sensitivity of these implants, to demonstrate improved resolution over competing technologies. These competing technologies, namely electrode-based retinal prostheses, utilize an artificial means to capture an image, convert that light energy into an electrical signal, and stimulate the remaining neural circuitry of a degenerated retina. There are several electrode-based retinal implants under development, with the most notable technologies being developed by Second Sight, Pixium Vision, and Retinal Implant AG. Despite improvements in the manufacturing of the electrode arrays, hardware interfaces, and surgical procedures, these retinal implants have intrinsic shortcomings. Most significantly, replicating the spatiotemporal patterns of the neurosensory network that facilitate normal visual perception is a challenge due to the small size requirements of electrodes needed for higher visual acuity. This problem is exacerbated by the limited resolution associated with the electrode arrays, resulting in only marginal improvement in visual acuity.

An important aspect of the protein-based prostheses of the present invention is the potential for restoring high-resolution vision, which is extremely difficult to achieve by electrode-based technologies. The directional gradient of protons used in the present invention to stimulate acid-sensing ion channels (ASICs) provides a unique approach to stimulating the bipolar and ganglion cells. However, because the mechanism of stimulation is through a directional ion cloud rather than direct contact with an electrode, the activation of the damaged neural network is complex and relies on multiple factors, including the molecular packing of the protein, the duration of the photocycle of BR, diffusion rates in the subretinal space, and the extent of lateral diffusion. We demonstrate here that the ion-mediated retinal implant is capable of the spatial sensitivity and temporal resolution necessary to facilitate a responsivity approaching native visual perception.

Additionally, these experiments have demonstrated the ability to monitor the temporal activation of these pH-mediated subretinal implants to show that the timing of RGC activation is on the order of ~150 ms, which is similar to native, uncompromised retinal tissue. We have also measured relative activation efficiencies of a 200-layer, protein-based retinal implant at light intensities of less than <7.2 mW/cm$^2$, which is similar to indoor ambient light intensities. Moreover, the results of a series of extracellular recording experiments using a multi-electrode array (MEA) quantified the spatial sensitivity and latencies of activation for the ion-mediated approach of stimulation of the present invention. Experiments have so far demonstrated that the protein-based retinal implant can stimulate the retina at light intensities comparable to indoor ambient light. To experimentally determine the extent to which lateral diffusion affects neighboring clusters of RGCs, a narrow beam of light (~200 μm FWHM diameter) was used to selectively activate the area around individual electrodes within a MEA. Our findings demonstrate high sensitivity with an upper limit of around 200 μm for the electrode separation chosen for the experiments. Further sensitivity can be achieved depending on the electrode separation and the array chosen.

Analysis of the Activation Efficiency and Temporal Resolution of the Retinal Implant:

Ex vivo extracellular recording experiments with P23H transgenic rats were employed to demonstrate the ability of an ion-mediated, protein-based prosthetic retina to stimulate the bipolar and ganglion cells of a degenerated retina. Extracellular recording experiments revealed that a 150-layer or 200-layer, BR based retinal implant can stimulate the degenerated retinas of P23H rat retinas. P23H-line 1 homozygous rats, which are models of the human form of autosomal dominant RP, were used in this investigation. The rats that were used ranged in age from 8-12 months, at which point a majority (>98%) of the photoreceptors are lost. The protocol for animal and tissue preparation is described in detail by Jensen and Rizzo. See, Jensen, R. J.; Rizzo III, J. F., Effects of Gaba Receptor Agonists on Thresholds of P23H Rat Retinal Ganglion Cells to Electrical Stimulation of the Retina. *J. Neural Eng.* 2011, 8, 1-8. After removal of the retina, the retinal implant was placed in a subretinal configuration and was oriented so that the directionality of proton pumping was either toward or away from the bipolar cells. RGCs are monitored for action potentials initiated by the retinal implant following the absorption of pulsed LED light. A single recording electrode was used during these studies, while a number of ganglion cells from multiple P23H rats were monitored to test the efficacy of the retinal implant architecture and temporal resolution.

Figure 3:
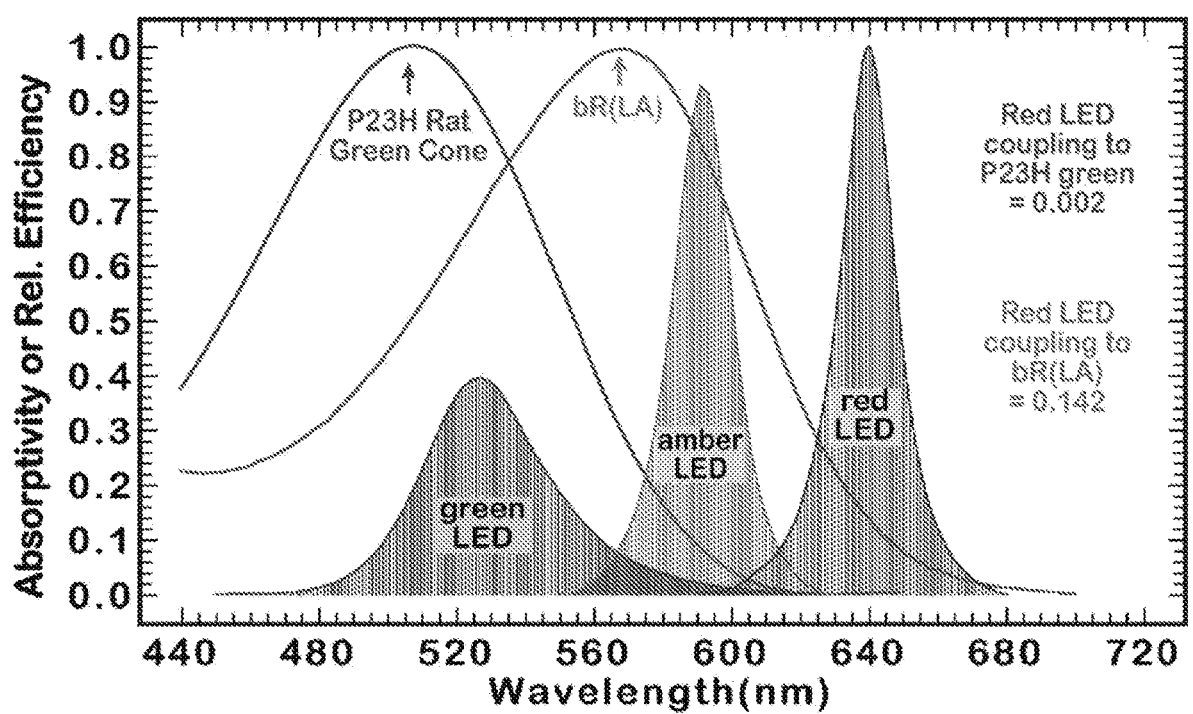
FIG. 3 shows a comparison of the absorption spectra of the P23H rat green cone pigment and light-adapted bacteriorhodopsin [bR(LA)] with the output from three LEDs used in the experiments. Note that the red LED couples with reasonable efficiency to the bR(LA) absorption spectrum, but poorly to the rat green cone. Because rats do not have red cones, and the P23H rat retina is degenerated, we can selectively activate the implant with red LEDs.

To stimulate the protein-based retinal implant and demonstrate that no remaining photoreceptor cells are responsible for absorbing incident light, a pulsed LED apparatus, was used to generate precise pulses of light energy at three wavelengths: green (530 nm), amber (590 nm), or red (630 nm), using pulse energies ranging from those simulating indoor, ambient light (7.2 mW/cm$^2$) to outdoor sunlight at noon (100 mW/cm$^2$) (FIG. 3). This pulsed LED apparatus interfaced with the neural monitoring electrophysiology equipment for selective stimulation of the retinal implant. To ensure that the signals generated were from the implant and not from the remaining photoreceptor cells, the retina was bleached with high intensity green light for 3 minutes. This step also had the advantage of light-adapting the BR within the implant, which improved the efficiency of proton pumping following light absorption. Next, the implant was pulsed with red light, which has a higher coupling efficiency with BR (0.173, FIG. 3) compared to the lower coupling efficiency with rat green cone pigments (0.004, FIG. 3). The bleaching process and the less effective coupling of red light with the remaining rat green cone pigments helps ensure that signals generated using red light are associated with the retinal implant.

Figure 4A:
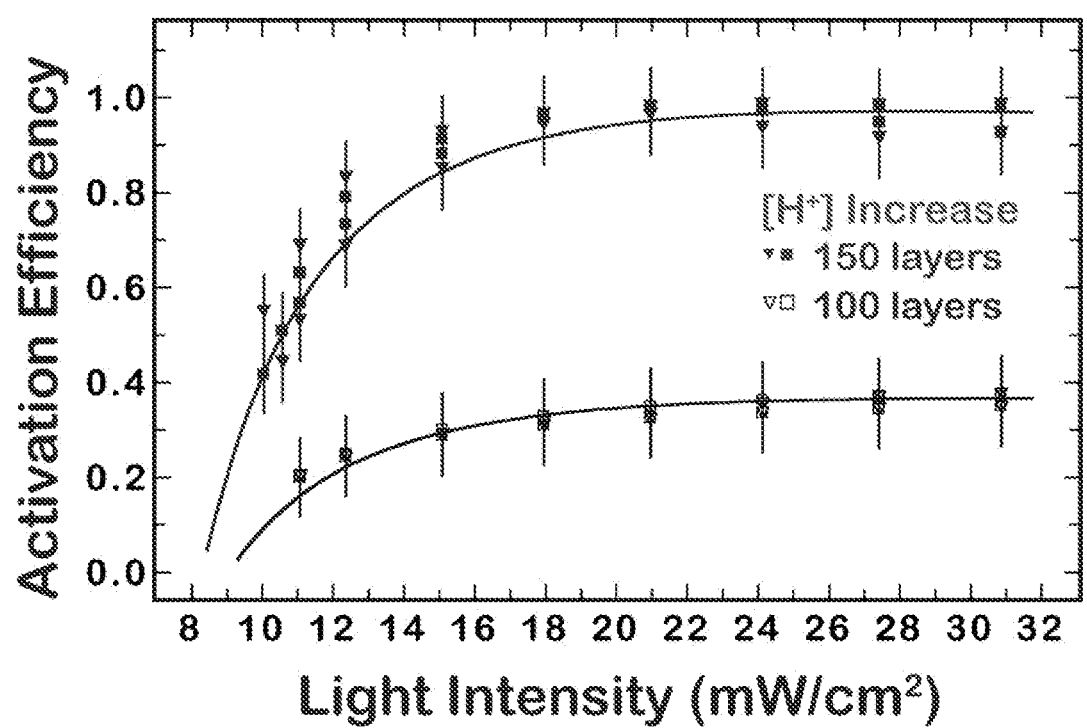
FIGS. 4A and 4B show the activation efficiency of excised P23H rat retinas in response to light activating the ion-mediated retinal implants.
Figure 4B:
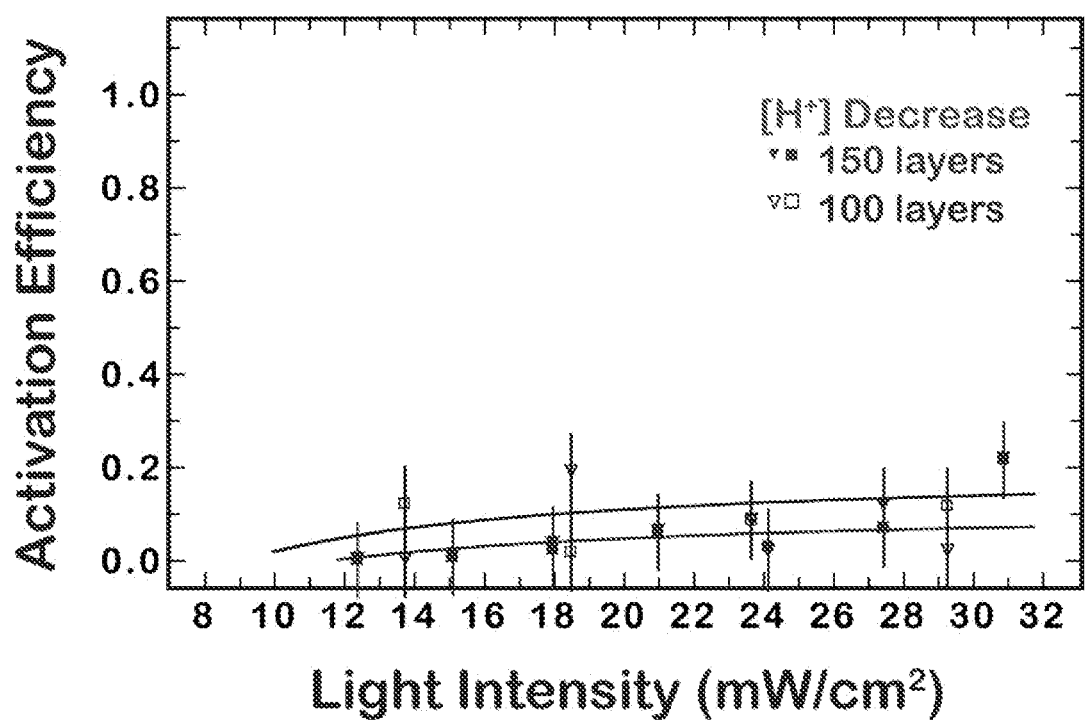
Figure 5A:
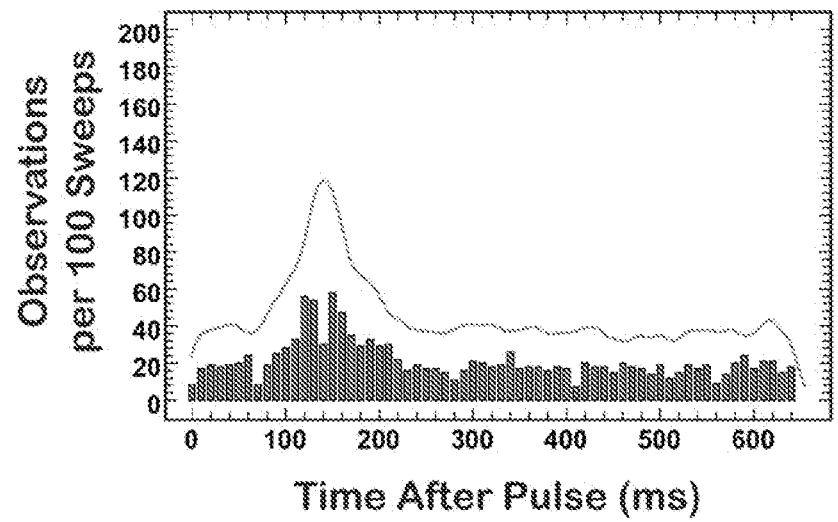
FIGS. 5A, 5B, 5C, 5D, 5E, and 5F show the distributions of latencies of measured RGCs of P23H rats following light activation of the retinal implant.
Figure 5B:
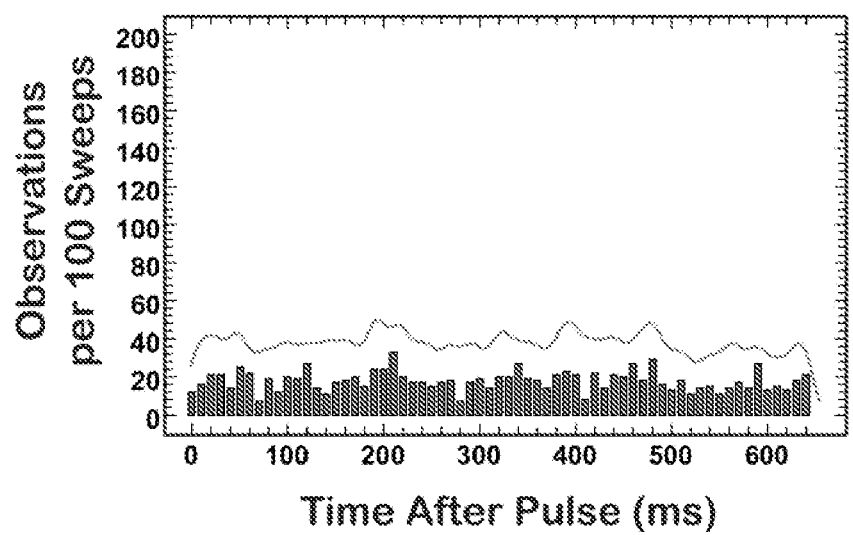
Figure 5C:
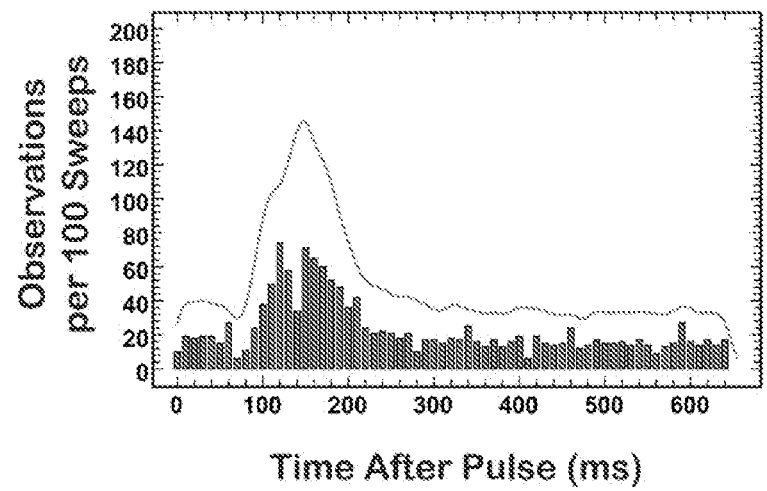
Figure 5D:
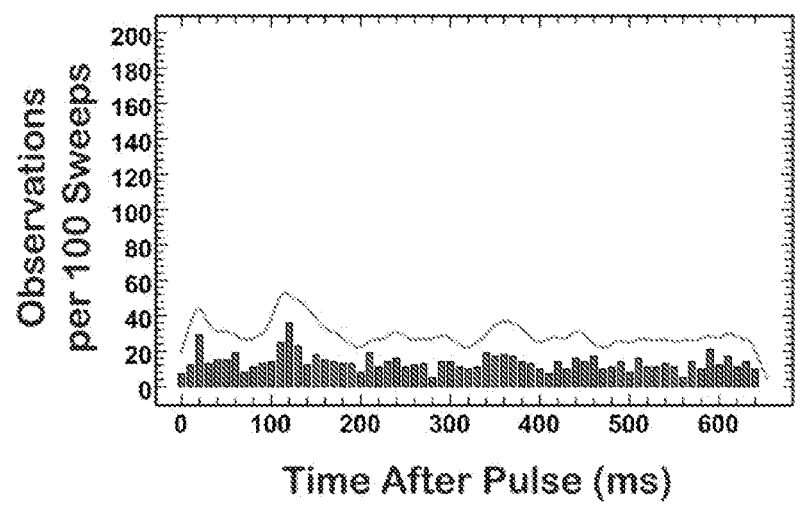
Figure 5E:
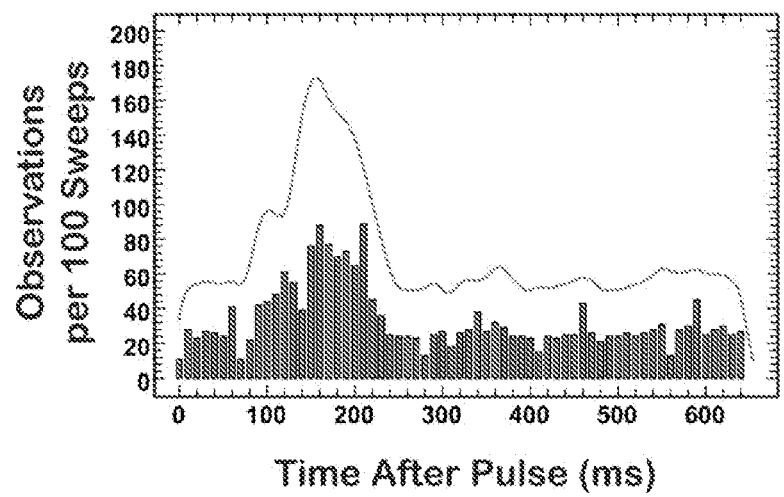
Figure 5F:
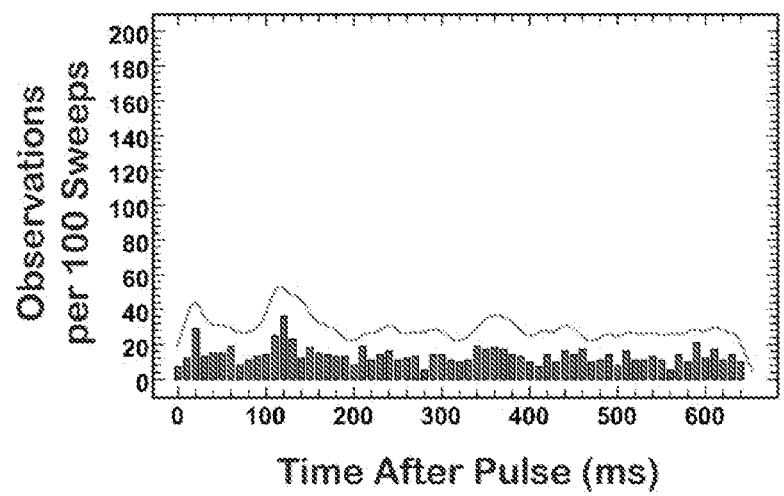

These results indicate that the retinal implant can reproducibly stimulate RGCs by modulating the pH surrounding the extracellular domain of remaining bipolar cells. The analysis required that the proper threshold (30 μV) was selected to differentiate between light-induced action potentials and background noise that is inherent to the degenerated retinas under investigation. The positive response generated by increasing [H$^+$] in the environment was facilitated through the activation of ASICs on these neural cells, causing a signal transduction cascade that has the potential to induce a visual percept. FIG. 4 presents a review of the data collected from these experiments with red light (630 nm) excitation, in which implants with various multilayer densities were positioned so that protons are pumped towards or away from the degenerated retinal tissue of the P23H rat. FIG. 4A shows that a high activation efficiency is achieved with increasing light intensity for the high OD (150 layer) implant, whereas the efficiency is cut in half with a low OD (100 layer) implant. This result further justifies that a sufficient number of layers is needed for reproducible activation. This minimum is generally about 150 to 200 layers. It should be appreciated that there is a balance between the minimum number of layers utilized and the reproducible activation to be achieved. Control experiments that decreased [H$^+$] (by reversing the orientation of the implant) generated little to no activation of the neural circuitry (FIG. 4B). This result is evident for both the high and low OD samples investigated in the study.

The data obtained in these single-recording experiments were also used to obtain a quantitative characterization of the temporal resolution of the retinal implant. The ~10 ms duration of the BR photocycle and the ability to modulate localized acidity makes the BR-based thin film an excellent candidate for an ion-mediated retinal implant. Lilley et al. have previously measured the threshold of proton-induced retinal stimulation at ~pH 6.5, and have demonstrated control of reproducible action potentials as acidic stimuli are pulsed at a millisecond time-scale. See, Lilley, S.; LeTissier, P.; Robbins, J., The Discovery and Characterization of a Proton-Gated Sodium Current in Rat Retinal Ganglion Cells. *J. Neurosci.* 2004, 24, 1013-1022; and Lilley, S.; Robbins, J., Characterisation of a Novel Proton-Gated Sodium Current in Rat Retinal Ganglion Cells. *J. Physiol.* 2001, 531, 83P-84P. However, the time course of activating ASICs is so far unknown, and the pH gradient generated by the retinal implant is very much dependent on light intensity and the duration of the incident light pulse. In other words, the BR contained within the protein layers may need to undergo multiple photocycles to build up sufficient $H^+$ ions around the bipolar cell environment. These experiments were undertaken to show that RGC activation occurred at a time scale relevant to facilitate visual acuity.

FIG. 5 presents a series of histograms showing the observed action potentials as a function of time following light activation. The number of observations was averaged per 100 measurements (or sweeps) after each 1 ms light pulse from a 630 nm light source, and a number of rats and ganglion cells were monitored to average the data. The traces in FIGS. 5A, 5C, and 5E summarize data for when the retinal implant was oriented in a direction that pumped protons towards the bipolar cells using a subretinal placement. The histograms show increasing activation with increasing light intensity (left panels, from top to bottom), which is similar to the activation efficiencies previously reported. The average latency of activation for each measured light intensity is ~150 ms, which is on the order of the temporal resolution with native, functional retinas. When the implant was placed in the opposite orientation (FIGS. 5B, 5D, and 5F) so that protons are pumped away from the retinal tissue, no apparent activation beyond the background noise that is present in all histograms that were plotted is observed. These results demonstrate that the timing of RGC activation achieved could support typical visual perception.

Figure 6A:
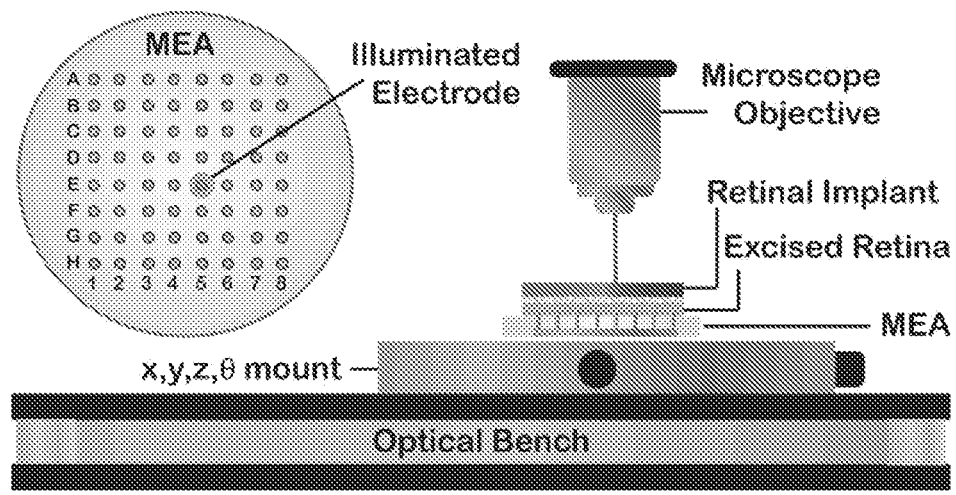
FIGS. 6A and 6B show a schematic of the multielectrode array (MEA) used for the extracellular recording experiments to quantify the spatial resolution of the protein-based retinal implant (FIG. 6A). Demonstration of selective activation of electrode 5 in row E of the 8×8 MEA (FIG. 6B). Light-induced action potentials are limited to the RGCs measured by electrode 5 within the array, whereas all other signals are due to spontaneous activity. The incident light beam has a diameter of 200 µm and was centered on electrode 5. The y-axis is the normalized amplitude of the irradiation beam and a normalized time range that spans 110.2 s.
Figure 7A:
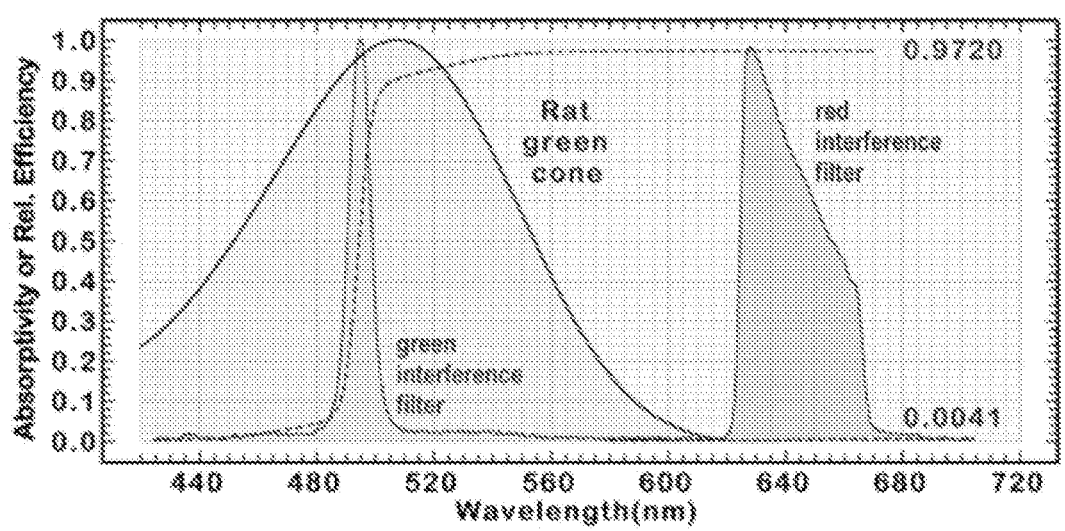
FIGS. 7A and 7B show a comparison of the absorption spectra of the P23H rat green cone (FIG. 7A) and light-adapted BR (bR.
Figure 7B:
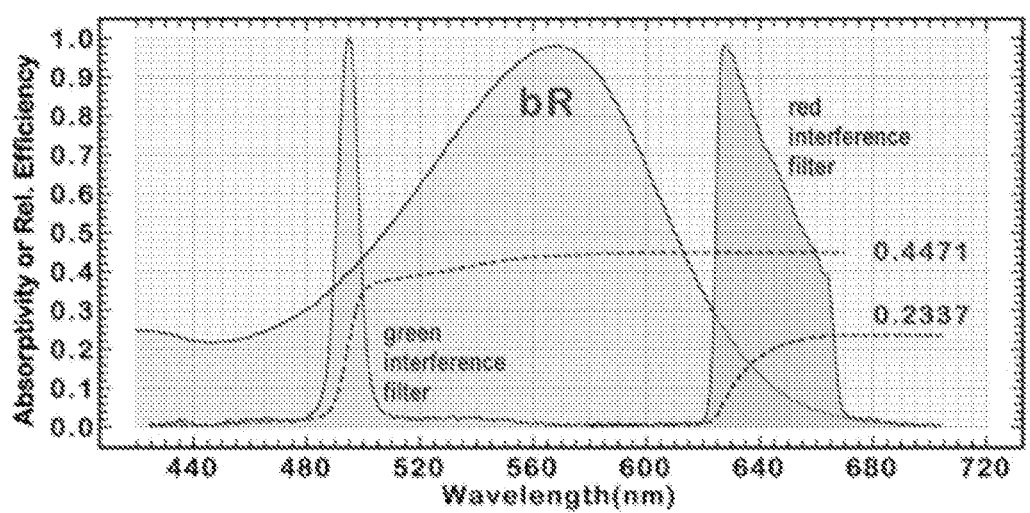

Thresholdinq and Activation Efficiency of the Protein-Based Retinal Implants Using a Multielectrode Array (MEA):

A series of experiments was performed using full field illumination to test the activation efficiency of the retinal implants, in which a multielectrode array (MEA) (30 μm electrode diameter, 200 μm separation, 8×8 rectangular grid) was used in place of the single electrode device, which permits monitoring 64 electrodes simultaneously (see FIG. 6A). The light source used for these experiments was modified such that the light beam is passed through a microscope objective directly above the excised retina/implant/MEA assembly. The full field illumination was provided by a light source projector employing a series of interference filters and neutral density filters to modulate the incident wavelength and light intensity, respectively. An iris aperture was also used to modulate the beam spot size, however, for this analysis, the entire array of electrodes was illuminated. FIG. 7 demonstrates the coupling efficiencies of the green and red interference filters with the spectrum of the rat green cone pigment and the spectrum of BR. Pulsed red light is used to selectively activate BR (FIG. 7B; coupling efficiency=0.2337) of any remaining green cones (FIG. 7A; coupling efficiency=0.0041) within the degenerated retina. Consequently, any activation measured by the MEA was likely induced via the ion gradient generated by the BR-based implant.

P23H rat retinas were excised as in the experiments described above. The previous experiments have confirmed the performance efficacy of the orientation of the 150-layer to 200-layer protein-based retinal implant using an ex vivo extracellular recording. Pulsed red light (100 ms pulse, 640 nm) was used to activate the full field of electrodes within the electrode array.

Determining the Spatial Resolution of a Retinal Implant Using a Multielectrode Array (MEA):

The spatial sensitivity of a retinal implant of the present invention was determined by reducing the beam spot used for full field stimulation to only activate single electrodes within the electrode array (see FIG. 6A). This reduction was performed using an iris aperture and a microscope objective to localize the incident beam. An x,y,z θ mount was also used to position the beam spot with high selectivity. Because the electrode diameter used was 30 μm and the separation between each electrode was 200 μm, individual electrodes were targeted with a light beam with a 200 μm diameter and the entire electrode array was monitored simultaneously, with the expectation that unilluminated electrodes would exhibit no change in activity. The beam was then moved between adjacent electrodes to further demonstrate responsivity and resolution.

Figure 8A:
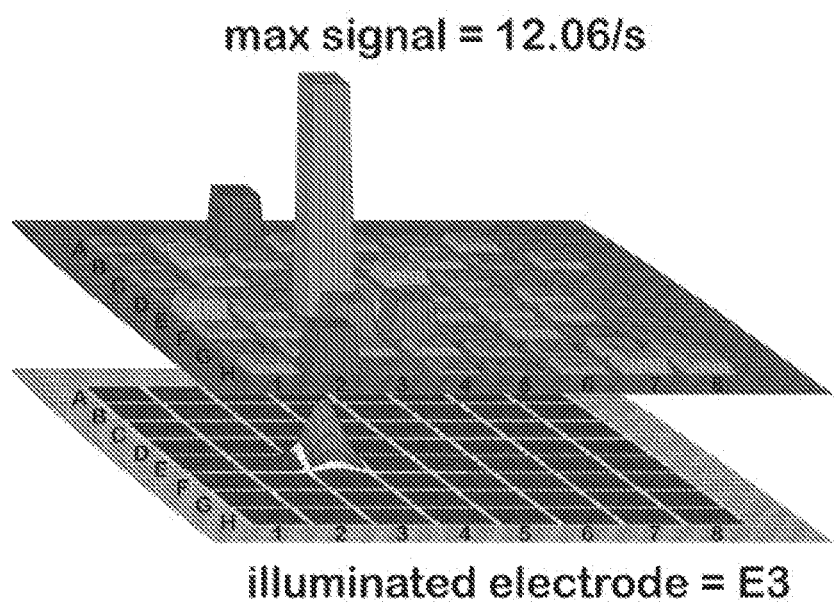
FIGS. 8A, 8B, and 8C show targeted illumination of a P23H rat retina centered on a single electrode within an MEA array.
Figure 8B:
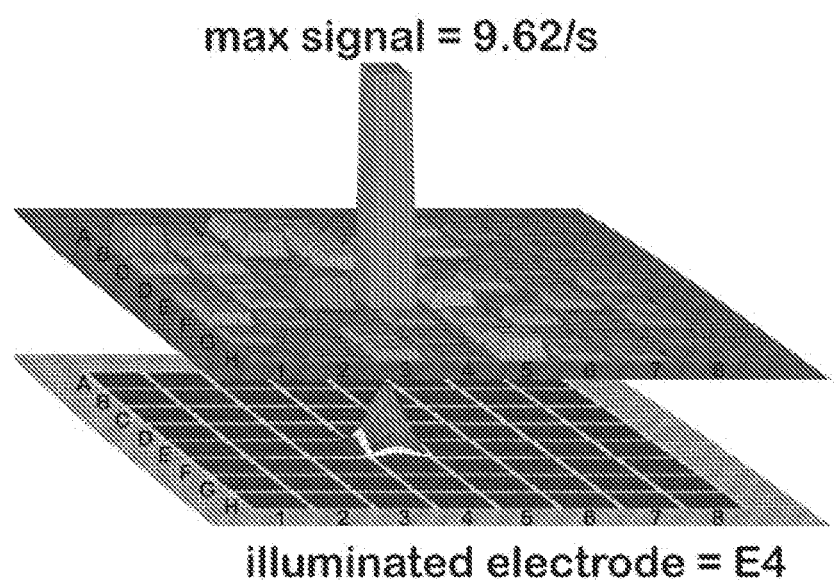
Figure 8C:
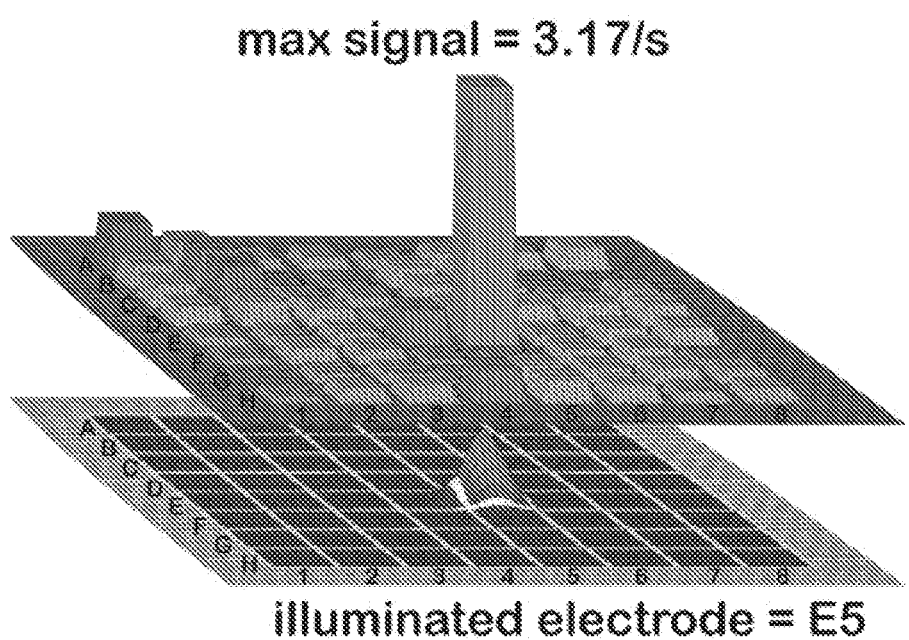

The results shown in FIG. 8 are for a contiguous set of three electrodes within the MEA. Throughout the course of these measurements, the illuminated electrode was translated along row E in the 8×8 MEA. The spot size of the red LED had a diameter of ~200 μm, and a full width at half maximum (FWHM), equivalent to the separation distance between electrodes. The location of illumination is represented in the lower plot of each panel in the figure. The upper plot of each panel shows the relative activation rate (signals/seconds) for each electrode within the MEA. FIG. 8A demonstrates that when only electrode E3 was illuminated, the RGCs activation was localized to that one spot which was dominated by a high relative signal rate. Some activity was observed adjacent to and farther away from electrode E3, however, this activity was likely due to spontaneous activity within the retina during the collection period. When the beam spot was translated to electrodes E4 and E5 (FIGS. 8B and 8C, respectively), the result was reproduced with the electrode of interest measuring the highest activation rate with little to no signal observed elsewhere.

FIG. 8 shows the maximum signal rate represented by the normalized signals in each panel. Electrodes E3, E4, and E5 measured signal rates of 12.06/s, 9.62/s, and 3.17/s, respectively. Each of the plots were normalized to the maximum signal rate (signals/seconds) of the illuminated electrode. The maximum rate observed does not directly correlate with the maximum noise observed in each panel, nor do these rates correlate to the relative efficiency of RGCs.

Figure 6B:
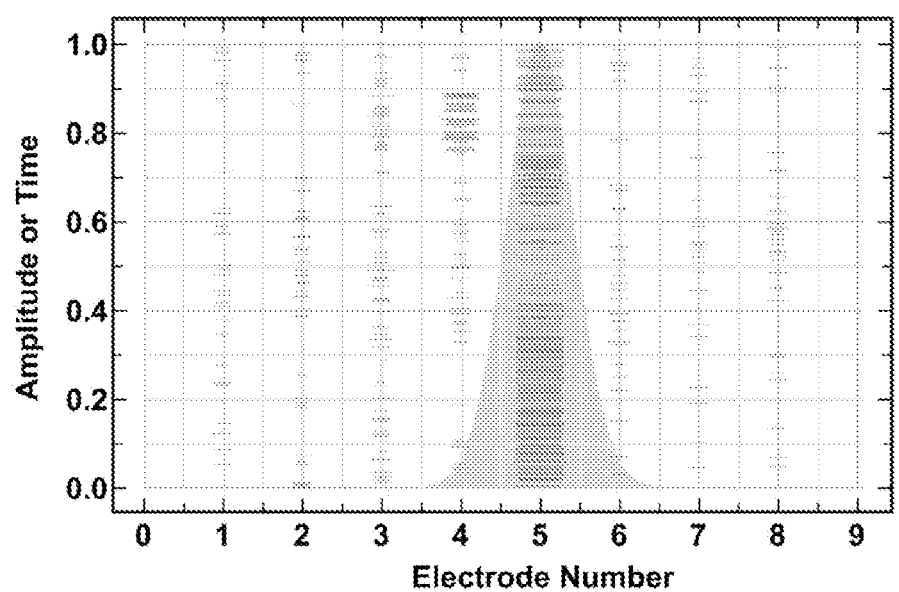

FIG. 6B further demonstrates the spatial sensitivity effect from a plot of the action potentials throughout a normalized duration of time (110.2 seconds), while electrode E5 in an 8-electrode row array (row E) was targeted with a narrow beam of light (~200 μm in diameter) to selectively activate the RGCs in contact with this electrode. The light-activated action potentials measured from the ganglion cells were shown to be localized to this one electrode, with little to no activity observed on adjacent electrodes. Because only targeted neurons in contact with a single electrode showed a light response, it can be estimated that the RGC collecting area has an upper limit of 200 μm in diameter. These results support that, the ion gradient that was generated was localized to the illuminated region of the retinal implant. The maximum area of sensitivity was measured at 200 μm in diameter, corresponding to the minimum separation of electrodes within the apparatus. These results also validated that lateral diffusion at the interface of the retinal implant and that the bipolar cells were minimized and not impacting surrounding neural tissue during light activation, and that the implant can produce near diffraction limited resolution.

These results demonstrate that the protein-based retinal implants of the present invention are capable of achieving increased spatial resolution versus electrode-based retinal implants.

Stimulation of Retinal Cells

Methods:

Retinal implant constructs, comprised of an ion permeable membrane and alternating layers of BR and a polycation binder, were manufactured using layer-by-layer electrostatic adsorption. Upon the absorption of light, the BR layers generate a unidirectional proton gradient that activates ASICs present in the outer membrane of bipolar and ganglion cells. The retinal implants were placed in a subretinal position relative to the excised retina of P23H transgenic rats, and a pulsed LED system was used to generate precise pulses at a wavelength that selectively activates BR. Extracellular recording, using both a single electrode and multielectrode array, was carried out to validate the ion-mediated mechanism of action and to investigate the spatial sensitivity of the retinal prosthetic.

The retinal implants useful herein and the bacteriorhodopsin mutants are further described in U.S. Pat. No. 8,563,026 B2, to Birge et al., issued Oct. 22, 2013 and U.S. Pat. No. 8,883,719 B2, to Birge et al., issued Nov. 11, 2014, which are incorporated by reference herein in their entirety.

Results: Studies using extracellular recording of retinal ganglion cells in excised P23H rat retinas indicate that the subretinal implant of the present invention is capable of stimulating the retinal tissue via a directional proton gradient. The activation efficiency of the protein-based prosthetic increases with the increasing intensity of incident red light (~640 nm). The experiments suggest that the implant can stimulate the retina using light intensities that are comparable to indoor ambient light (~7.2 mW/cm$^2$), and also demonstrate that the temporal resolution of the prosthetic is similar to a physiological latency of activation (~150 ms). Moreover, a multielectrode array is used to show that activation can be focused to a 200-μm pixel diameter. These results show that a BR-based retinal implant can stimulate the remaining neural circuitry of P23H retinas, demonstrating the potential efficacy in the treatment for AMD and RP.

INCORPORATION BY REFERENCE

The entire disclosure of each of the patent documents, including certificates of correction, patent application documents, scientific articles, governmental reports, websites, and other references referred to herein is incorporated by reference herein in its entirety for all purposes. In case of a conflict in terminology, the present specification controls.

EQUIVALENTS

The invention can be embodied in other specific forms without departing from the spirit or essential characteristics thereof. The foregoing embodiments are to be considered in all respects illustrative rather than limiting on the invention described herein. In the various embodiments of the present invention, where the term comprises is used, it is also contemplated that the embodiments consist essentially of, or consist of, the recited steps or components. Furthermore, the order of steps or the order for performing certain actions is immaterial as long as the invention remains operable. Moreover, two or more steps or actions can be conducted simultaneously.

In the specification, the singular forms also include the plural forms, unless the context clearly dictates otherwise. Unless defined otherwise, all technical and scientific terms used herein have the same meaning as commonly understood by one of ordinary skill in the art to which this invention belongs. In the case of conflict, the present specification will control.

What is claimed is:

1. A method for treating a patient having loss of vision caused by loss of retinal cells, comprising,
   (a) implanting into an eye of the patient a bacteriorhodopsin-based retinal implant, and
   (b) activating the implant with a light source,
   wherein the implant stimulates retinal cells such that the stimulation is provided at a resolution with pixel dimensions less than about 500 μm, or less than about 350 μm, or less than about 250 μm, or less than about 200 μm, or less than about 150 μm, or less than about 100 μm, or less than about 75 μm, or less than about 50 μm, or less than about 40 μm, or less than about 30 μm, or less than about 25 μm.

2. The method according to claim 1, wherein the bacteriorhodopsin-based retinal implant, comprises at least one substrate layer and a bacteriorhodopsin film, wherein the bacteriorhodopsin film comprises a plurality of individual layers of a native bacteriorhodopsin or a bacteriorhodopsin mutant, wherein each individual layer of the native bacteriorhodopsin or bacteriorhodopsin mutant alternates with a layer of a cationic polymer, and wherein the bacteriorhodopsin mutant is selected from the group consisting of a chloride pump mutant, a dipole mutant, a photocycle mutant, a gold-binding mutant, an ion pump mutant, a Q-state mutant, and combinations thereof.

3. The method according to claim 2, wherein the light source is a light source emitting human visible wavelengths, i.e. about 400 to about 700 nm.

4. The method according to claim 3 wherein the light source is a pulsed light source.

5. The method according to claim 3 wherein the light source is a continuous light source.

6. The method according to claim 2 wherein the light source has an intensity less than about 100 mW/cm$^2$, 50 mW/cm$^2$, 40 mW/cm$^2$, or less than about 30 mW/cm$^2$, or less than about 20 mW/cm$^2$, or less than about 10 mW/cm$^2$, or less than about 5 mW/cm$^2$, or less than about 1 mW/cm$^2$.

7. The method according to claim 2 wherein the substrate layer is an ion permeable layer and is on one or both sides of the implant.

8. The method according to claim 7, wherein the substrate layer is selected from polyethylene terephthalate (PET), 2-hydroxyethyl methacrylate (HEMA), 2-phenylethyl methacrylate (PEM), polyethylene glycol (PEG), methyl methacrylate (MMA), polydimethylsiloxane (PDMS) macromer, poly(vinyl pyrrolidone) (PVP), poly(p-xylylene) (also known as parylene), polyvinyl alcohol (PVA) hydrogel, and combinations thereof.

9. The method according to 7 wherein the substrate layer is less than 100 μm in thickness and contains an evenly distributed array of apertures of a diameter less than about 100 μm.

10. The method according to claim 1 wherein the implant is a biocompatible, ion permeable retinal implant.

11. The method according to claim 1 wherein the implant is implanted in a position selected from a subretinal position or an epiretinal position.

12. The method according to claim 1 wherein the retinal cells are selected from retinal ganglion cells, retinal bipolar cells, retinal photoreceptor cells, and combinations thereof.

13. The method according to claim 1 wherein the retinal implant comprises at least about 100 layers of a native bacteriorhodopsin or a bacteriorhodopsin mutant, or at least about 150 layers of a native bacteriorhodopsin or a bacteriorhodopsin mutant, or at least about 200 layers of a native bacteriorhodopsin or a bacteriorhodopsin mutant.

14. The method according to claim 1 wherein the retinal implant further provides a temporal resolution of at least about 30 milliseconds.

15. The method according to claim 1, wherein the retinal implant initiates to the cells an action potential of about 40 μV.

16. The method according to claim 1 wherein the retinal implant provides a unidirectional proton gradient.

17. The method according to claim 16 wherein the bacteriorhodopsin-based retinal implant comprises bacteriorhodopsin molecules such that they are uniformly oriented.

18. The method according to claim 1 wherein the vision loss is caused by loss of retinal photoreceptor cells.

19. The method according to claim 1 wherein the bacteriorhodopsin-based retinal implant is based on native bacteriorhodopsin.

20. The method according to claim 1 wherein the bacteriorhodopsin-based retinal implant is based on a bacteriorhodopsin mutant.

21. The method according to claim 20 wherein the mutant is a Q-state mutant.

22. A method for treating a patient having loss of vision caused by loss of retinal cells, comprising,
(a) implanting into an eye of the patient a bacteriorhodopsin-based retinal implant, and
(b) activating the implant with a light source,
wherein the implant stimulates retinal cells such that the stimulation is provided at a resolution limited by (i) the diffraction limit of the light source or (ii) when the retinal implant further comprises an ion-permeable substrate, the aperture diameter and density of the ion-permeable substrate.

23. A method for treating a patient having loss of vision caused by loss of retinal cells, comprising,
(a) implanting into an eye of the patient a bacteriorhodopsin-based retinal implant, and
(b) activating the implant with a light source,
wherein the implant stimulates retinal cells such that the stimulation is provided at a resolution with a pixel density of about 4 pixels/mm$^2$ and pixel dimension of about 500 μm, or with a pixel density of about 8 pixels/mm$^2$ and pixel diameter of about 350 μm, or with a pixel density of about 16 pixels/mm$^2$ and pixel diameter of about 250 μm, or with a pixel density of about 25 pixels/mm$^2$ and pixel diameter of about 200 μm, or with a pixel density of about 44 pixels/mm$^2$ and pixel diameter of about 150 μm, or with a pixel density of about 100 pixels/mm$^2$ and pixel diameter of about 100 μm, or with a pixel density of about 178 pixels/mm$^2$ and pixel diameter of about 75 μm, or with a pixel density of about 400 pixels/mm$^2$ and pixel diameter of about 50 μm, or with a pixel density of about 625 pixels/mm$^2$ and pixel diameter of about 40 μm, or with a pixel density of about 1111 pixels/mm$^2$ and pixel diameter of about 30 μm, or with a pixel density of about 1600 pixels/mm$^2$ and pixel diameter of about 25 μm.

24. A method for stimulating retinal cells comprising,
(a) contacting the retinal cells with a bacteriorhodopsin-based retinal implant,
(b) activating the implant with a light source,
wherein
(i) wherein the implant stimulates retinal cells such that the stimulation is provided at a resolution with pixel dimensions less than about 500 μm, or less than about 350 μm, or less than about 250 μm, or less than about 200 μm, or less than about 150 μm, or less than about 100 μm, or less than about 75 μm, or less than about 50 μm, or less than about 40 μm, or less than about 30 μm, or less than about 25 μm; or
(ii) wherein the implant stimulates retinal cells such that the stimulation is provided at a resolution limited by (a) the diffraction limit of the light source or (b) when the retinal implant further comprises an ion-permeable substrate, the aperture diameter and density of the ion-permeable substrate; or
(iii) wherein the implant stimulates retinal cells such that the stimulation is provided at a resolution with a pixel density of about 4 pixels/mm$^2$ and pixel dimension of about 500 μm, or with a pixel density of about 8 pixels/mm$^2$ and pixel diameter of about 350 μm, or with a pixel density of about 16 pixels/mm$^2$ and pixel diameter of about 250 μm, or with a pixel density of about 25 pixels/mm$^2$ and pixel diameter of about 200 μm, or with a pixel density of about 44 pixels/mm$^2$ and pixel diameter of about 150 μm, or with a pixel density of about 100 pixels/mm$^2$ and pixel diameter of about 100 μm, or with a pixel density of about 178 pixels/mm$^2$ and pixel diameter of about 75 μm, or with a pixel density of about 400 pixels/mm$^2$ and pixel diameter of about 50 μm, or with a pixel density of about 625 pixels/mm$^2$ and pixel diameter of about 40 μm, or with a pixel density of about 1111 pixels/mm$^2$ and pixel diameter of about 30 μm, or with a pixel density of about 1600 pixels/mm$^2$ and pixel diameter of about 25 μm.

25. A retinal implant for treating a patient having loss of vision caused by loss of retinal cells, comprising, (i) a retinal implant that when activated by a light source stimulates retinal cells such that the stimulation is provided at a resolution with pixel dimensions less than about 500 μm, or less than about 350 μm, or less than about 250 μm, or less than about 200 μm, or less than about 150 μm, or less than about 100 μm, or less than about 75 μm, or less than about 50 μm, or less than about 40 μm, or less than about 30 μm, or less than about 25 μm, or
(ii) a retinal implant for treating a patient having loss of vision caused by loss of retinal cells, comprising, a retinal implant that when activated by a light source stimulates retinal cells such that the stimulation is provided at a resolution limited by (a) the diffraction limit of the light source or (b) when the retinal implant further comprises an ion-permeable substrate, the aperture diameter and density of the ion-permeable substrate, or
(iii) a retinal implant for treating a patient having loss of vision caused by loss of retinal cells, comprising, a retinal implant that when activated by a light source stimulates retinal cells such that the stimulation is provided at a resolution with a pixel density of about 4 pixels/mm$^2$ and pixel dimension of about 500 μm, or with a pixel density of about 8 pixels/mm$^2$ and pixel diameter of about 350 μm, or with a pixel density of about 16 pixels/mm$^2$ and pixel diameter of about 250 μm, or with a pixel density of about 25 pixels/mm$^2$ and pixel diameter of about 200 μm, or with a pixel density of about 44 pixels/mm$^2$ and pixel diameter of about 150 μm, or with a pixel density of about 100 pixels/mm$^2$ and pixel diameter of about 100 μm, or with a pixel density of about 178 pixels/mm$^2$ and pixel diameter of about 75 μm, or with a pixel density of about 400 pixels/mm$^2$ and pixel diameter of about 50 μm, or with a pixel density of about 625 pixels/mm$^2$ and pixel diameter of about 40 μm, or with a pixel density of about 1111 pixels/mm$^2$ and pixel diameter of about 30 μm, or with a pixel density of about 1600 pixels/mm$^2$ and pixel diameter of about 25 μm, wherein the implant is a bacteriorhodopsin-based retinal implant that comprises at least one substrate layer and a bacteriorhodopsin film, wherein the bacteriorhodopsin film comprises a plurality of individual layers of a native bacteriorhodopsin or a bacteriorhodopsin mutant, wherein each individual layer of the native bacteriorhodopsin or bacteriorhodopsin mutant alternates with a layer of a cationic polymer, and wherein the bacteriorhodopsin mutant is selected from the group consisting of a chloride pump mutant, a dipole mutant, a photocycle mutant, a gold-binding mutant, an ion pump mutant, a Q-state mutant, and combinations thereof.

26. The retinal implant according to claim 25, wherein the light source is a light source emitting human visible wavelengths, i.e. about 400 to about 700 nm.

27. The retinal implant according to claim 26 wherein the light source is selected from a pulsed light source or a continuous light source.

28. The retinal implant according to claim 25 wherein the light source has an intensity less than about 100 mW/cm$^2$, 50 mW/cm$^2$, 40 mW/cm$^2$, or less than about 30 mW/cm$^2$, or less than about 20 mW/cm$^2$, or less than about 10 mW/cm$^2$, or less than about 5 mW/cm$^2$, or less than about 1 mW/cm$^2$.

29. The retinal implant according to claim 25 wherein the implant is a biocompatible, ion permeable retinal implant.

30. The A retinal implant according to claim 25 wherein the implant is implanted in a position selected from a subretinal position or an epiretinal position.

31. The retinal implant according to claim 25 wherein the retinal cells are selected from retinal ganglion cells, retinal bipolar cells, retinal photoreceptor cells, and combinations thereof.

32. The retinal implant according to claim 25 wherein the retinal implant comprises at least about 100 layers of a native bacteriorhodopsin or a bacteriorhodopsin mutant, or at least about 150 layers of a native bacteriorhodopsin or a bacteriorhodopsin mutant, or at least about 200 layers of a native bacteriorhodopsin or a bacteriorhodopsin mutant.

33. The retinal implant according to claim 25 wherein the retinal implant further provides a temporal resolution of at least about 30 milliseconds.

34. The retinal implant according to claim 25, wherein the retinal implant initiates to the cells an action potential of about 40 μV.

35. The retinal implant according to claim 25 wherein the retinal implant provides a unidirectional proton gradient.

36. The retinal implant according to claim 35 wherein the retinal implant comprises bacteriorhodopsin molecules such that they are uniformly oriented.

37. The retinal implant according to claim 25 wherein the vision loss is caused by loss of retinal photoreceptor cells.

38. The retinal implant according to claim 25 wherein the substrate layer is an ion permeable layer and is on one or both sides of the implant.

39. The retinal implant according to claim 38, wherein the substrate layer is selected from polyethylene terephthalate (PET), 2-hydroxyethyl methacrylate (HEMA), 2-phenylethyl methacrylate (PEM), polyethylene glycol (PEG), methyl methacrylate (MMA), polydimethylsiloxane (PDMS) macromer, poly(vinyl pyrrolidone) (PVP), poly(p-xylylene) (also known as parylene), polyvinyl alcohol (PVA) hydrogel, and combinations thereof.

40. The retinal implant according to 38 wherein the substrate layer is less than 100 μm in thickness and contains an evenly distributed array of apertures of a diameter less than about 100 μm.

41. The retinal implant according to claim 25 wherein the retinal implant is based on native bacteriorhodopsin.

42. The retinal implant according to claim 25 wherein the retinal implant is based on a bacteriorhodopsin mutant.

43. The retinal implant according to claim 42 wherein the mutant is a Q-state mutant.

44. A retinal implant for treating a patient having loss of vision caused by loss of retinal cells, comprising, a retinal implant that when activated by a light source stimulates retinal cells such that the stimulation is provided at a resolution with pixel dimensions less than about 500 μm, or less than about 350 μm, or less than about 250 μm, or less than about 200 μm, or less than about 150 μm, or less than about 100 μm, or less than about 75 μm, or less than about 50 μm, or less than about 40 μm, or less than about 30 μm, or less than about 25 μm, wherein the implant is a bacteriorhodopsin-based retinal implant that comprises at least one substrate layer and a bacteriorhodopsin film, wherein the bacteriorhodopsin film comprises a plurality of individual layers of a native bacteriorhodopsin or a bacteriorhodopsin mutant, wherein each individual layer of the native bacteriorhodopsin or bacteriorhodopsin mutant alternates with a layer of a cationic polymer, and wherein the bacteriorhodopsin mutant is selected from the group consisting of a chloride pump mutant, a dipole mutant, a photocycle mutant, a gold-binding mutant, an ion pump mutant, a Q-state mutant, and combinations thereof.

45. A retinal implant for treating a patient having loss of vision caused by loss of retinal cells, comprising, a retinal implant that when activated by a light source stimulates retinal cells such that the stimulation is provided at a resolution limited by (a) the diffraction limit of the light source or (b) when the retinal implant further comprises an ion-permeable substrate, the aperture diameter and density of the ion-permeable substrate, wherein the implant is a bacteriorhodopsin-based retinal implant that comprises at least one substrate layer and a bacteriorhodopsin film, wherein the bacteriorhodopsin film comprises a plurality of individual layers of a native bacteriorhodopsin or a bacteriorhodopsin mutant, wherein each individual layer of the native bacteriorhodopsin or bacteriorhodopsin mutant alternates with a layer of a cationic polymer, and wherein the bacteriorhodopsin mutant is selected from the group consisting of a chloride pump mutant, a dipole mutant, a photocycle mutant, a gold-binding mutant, an ion pump mutant, a Q-state mutant, and combinations thereof.

46. A retinal implant for treating a patient having loss of vision caused by loss of retinal cells, comprising, a retinal implant that when activated by a light source stimulates retinal cells such that the stimulation is provided at a resolution with a pixel density of about 4 pixels/mm$^2$ and pixel dimension of about 500 μm, or with a pixel density of about 8 pixels/mm$^2$ and pixel diameter of about 350 μm, or with a pixel density of about 16 pixels/mm$^2$ and pixel diameter of about 250 μm, or with a pixel density of about 25 pixels/mm$^2$ and pixel diameter of about 200 μm, or with a pixel density of about 44 pixels/mm$^2$ and pixel diameter of about 150 μm, or with a pixel density of about 100 pixels/mm$^2$ and pixel diameter of about 100 μm, or with a pixel density of about 178 pixels/mm$^2$ and pixel diameter of about 75 μm, or with a pixel density of about 400 pixels/mm$^2$ and pixel diameter of about 50 μm, or with a pixel density of about 625 pixels/mm$^2$ and pixel diameter of about 40 μm, or with a pixel density of about 1111 pixels/mm$^2$ and pixel diameter of about 30 μm, or with a pixel density of about 1600 pixels/mm$^2$ and pixel diameter of about 25 μm, wherein the implant is a bacteriorhodopsin-based retinal implant that comprises at least one substrate layer and a bacteriorhodopsin film, wherein the bacteriorhodopsin film comprises a plurality of individual layers of a native bacteriorhodopsin or a bacteriorhodopsin mutant, wherein each individual layer of the native bacteriorhodopsin or bacteriorhodopsin mutant alternates with a layer of a cationic polymer, and wherein the bacteriorhodopsin mutant is selected from the group consisting of a chloride pump mutant, a dipole mutant, a photocycle mutant, a gold-binding mutant, an ion pump mutant, a Q-state mutant, and combinations thereof.

\* \* \* \* \*